United States Patent
Ganguly et al.

(10) Patent No.: US 11,147,971 B2
(45) Date of Patent: Oct. 19, 2021

(54) SYSTEMS METHODS AND DEVICES FOR CLOSED LOOP STIMULATION TO ENHANCE STROKE RECOVERY

(71) Applicant: Regents of the University of California, San Francisco, CA (US)

(72) Inventors: Karunesh Ganguly, San Francisco, CA (US); Tanuj Gulati, San Francisco, CA (US); Dhakshin Ramanathan, San Francisco, CA (US)

(73) Assignee: The Regents of the University of California, San Francisco, CA (US)

(*) Notice: Subject to any disclaimer, the term of this patent is extended or adjusted under 35 U.S.C. 154(b) by 32 days.

(21) Appl. No.: 16/311,309

(22) PCT Filed: Jun. 26, 2017

(86) PCT No.: PCT/US2017/039293
§ 371 (c)(1),
(2) Date: Dec. 19, 2018

(87) PCT Pub. No.: WO2017/223564
PCT Pub. Date: Dec. 28, 2017

(65) Prior Publication Data
US 2019/0232061 A1    Aug. 1, 2019

Related U.S. Application Data

(60) Provisional application No. 62/354,543, filed on Jun. 24, 2016.

(51) Int. Cl.
*A61N 1/36* (2006.01)
*A61N 1/05* (2006.01)
*A61N 1/20* (2006.01)

(52) U.S. Cl.
CPC ....... *A61N 1/36103* (2013.01); *A61N 1/0529* (2013.01); *A61N 1/20* (2013.01);
(Continued)

(58) Field of Classification Search
CPC ............ A61N 1/36103; A61N 1/36031; A61N 1/0529; A61N 1/20; A61N 1/36003; A61N 1/36017; A61N 1/36025; A61N 1/36135
(Continued)

(56) References Cited

U.S. PATENT DOCUMENTS 9,113,912 B1 * 8/2015 Mehta ............... A61B 18/1492
2006/0015153 A1   1/2006 Gliner et al.
(Continued)

FOREIGN PATENT DOCUMENTS

WO    2007138598 A2    12/2007
WO    WO2007/138598  * 12/2007
WO    2015069632       5/2015

OTHER PUBLICATIONS

Tanuj Gulati et al., "Robust Neuroprosthetic Control from the Stroke Perilesional Cortex", "The Journal of Neuroscience", Jun. 3, 2015, pp. 8653-8661, vol. 35, No. 22.
(Continued)

*Primary Examiner* — Erin M Piateski
(74) *Attorney, Agent, or Firm* — Dentons Davis Brown, P.C.; Matthew Coryell

(57) ABSTRACT

Systems, methods and devices for promoting recovery from a stroke induced loss of motor function in a subject. In certain aspects, the system includes at least one electrode, and an operations system in electrical communication with at least one electrode, wherein the at least one electrode is constructed and arranged to apply current across the brain of the subject and to record low frequency oscillations from a
(Continued)

perilesional region of the subject. In certain aspects, provided is a method comprising placing at least one recording electrode in electrical communication in a perilesional region of the subject; placing at least one stimulation electrode in electrical communication with the brain of the subject; recording low frequency oscillations from the perilesional region of the subject; and delivering current stimulation to the brain of the subject.

18 Claims, 11 Drawing Sheets

(52) U.S. Cl.
CPC ..... *A61N 1/36003* (2013.01); *A61N 1/36017* (2013.01); *A61N 1/36025* (2013.01); *A61N 1/36031* (2017.08); *A61N 1/36135* (2013.01)

(58) Field of Classification Search
USPC .......................................................... 607/48
See application file for complete search history.

(56) References Cited

U.S. PATENT DOCUMENTS

| | | | |
|---|---|---|---|
| 2008/0114417 A1* | 5/2008 | Leyde ................ | A61N 1/36082 607/60 |
| 2010/0069995 A1* | 3/2010 | Danielsson ........ | A61N 1/36114 607/50 |
| 2011/0213440 A1 | 9/2011 | Fowler et al. | |
| 2011/0218588 A1* | 9/2011 | Jung ........................ | A61N 1/36 607/45 |
| 2016/0022168 A1* | 1/2016 | Luczak ................ | A61N 1/0534 600/544 |
| 2016/0220836 A1* | 8/2016 | Parks ................. | A61N 1/36021 |

OTHER PUBLICATIONS

Walter et al., "Dynamics of a Stimulation-evoked ECoG Potential During Stroke Rehabiliation—A Case Study", "Proceedings of the International Congress on Neurotechnology, Electronics and Informatics (BrainRehab-2013)", Jan. 1, 2013, pp. 241-248, Publisher: Science and Technology Publications, Lda.

* cited by examiner

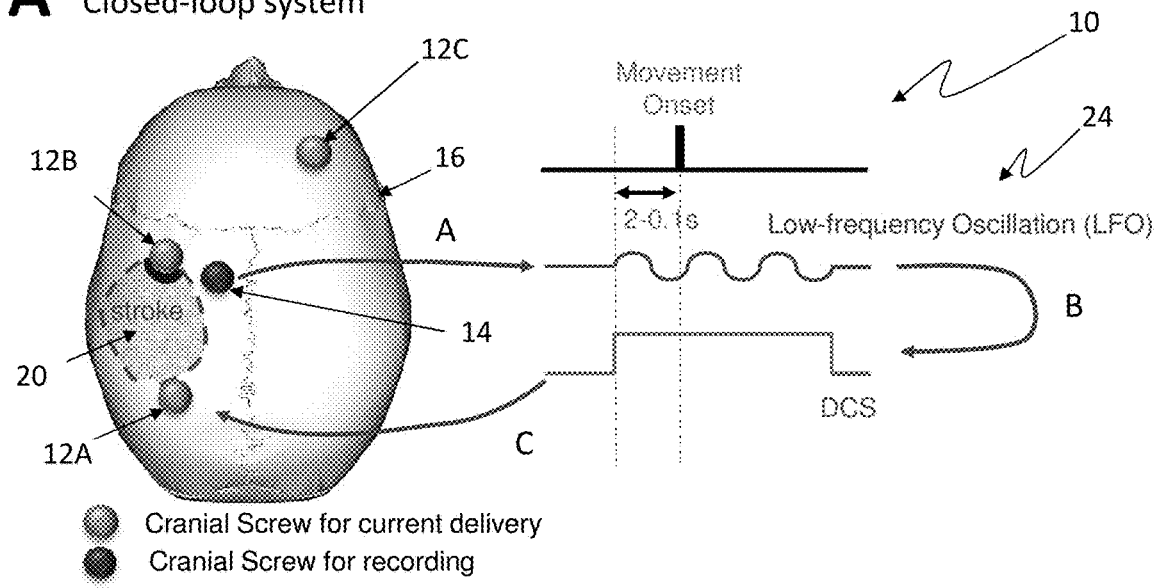
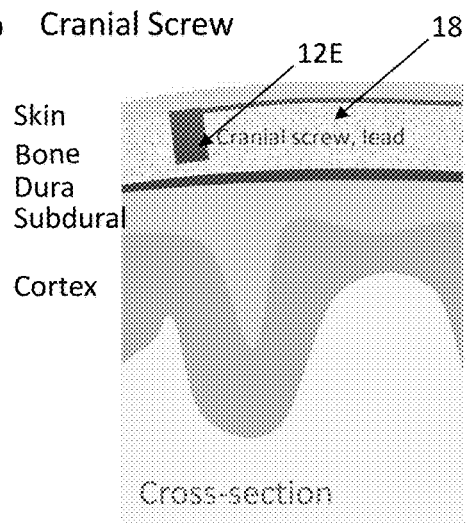
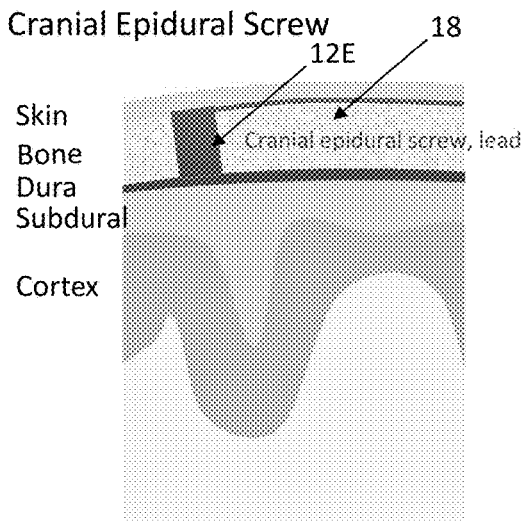
FIG. 1A-C

SYSTEMS METHODS AND DEVICES FOR CLOSED LOOP STIMULATION TO ENHANCE STROKE RECOVERY

CROSS-REFERENCE TO RELATED APPLICATION(S)

This application claims priority to International PCT Application No. PCT/US17/39293, filed on Jun. 24, 2017, which claims benefit of U.S. Provisional Application No. 62/354,543, filed on Jun. 24, 2016; which is incorporated herein by reference in its entirety.

BACKGROUND OF THE INVENTION

Stroke is the leading cause of motor disability in the United States, affecting over 700,000 patients each year. No pharmacological or mechanical therapies are currently approved to enhance function during recovery from stroke. Intensive physical therapy to help relearn and regain impaired motor functions is the only currently available treatment for stroke patients and often is a slow and incomplete process.

The development of novel technologies to promote motor rehabilitation after stroke would be very beneficial. From a network perspective, the motor system is a complex organization of interconnected nodes. This highly dynamic system is capable of generating finely coordinated actions as well as adapting to damage to the network. However, the electrophysiological correlates of the recovery process are poorly understood. For example, it remains unclear what electrophysiological patterns predict either recovery or the lack of recovery. Moreover, it remains unclear how to precisely modulate the motor network in order to improve function after injury.

Some neuromodulatory techniques (both invasive and non-invasive) have been studied for the purpose of promoting motor learning and stroke recovery. In these neuromodulation therapies, an electric or chemical signal stimulates nerve cell activity. Such therapies include transcranial direct current stimulation ("tCS"), transcranial magnetic stimulation ("TMS"), epidural cortical stimulation ("ECS"), and peripheral nerve stimulation ("PNS"). However, the results have shown inconsistent or marginal improvements in recovery. Further, the majority of these studies—including the tCS and TMS therapies—use an 'open-loop stimulation' design in which the electric stimulation is continuously turned on for an extended time period of preprogrammed and constant stimulation that is uncoupled to behavior or ongoing brain activity and thus does not respond to patient movement or symptoms. This constant, unvarying stimulation can deliver too much or too little stimulus and is not adaptable to the specific patient needs.

There is a need in the art for neurostimulation devices, systems, and methods for effective treatment of stroke patients.

BRIEF SUMMARY

Disclosed herein is a neurostimulation system for promoting subject recovery from a brain lesion that includes at least one electrode, and an operations system in electrical communication with at least one electrode, wherein the at least one electrode is constructed and arranged to apply current across the brain of the subject and to record low frequency oscillations from a perilesional region of the subject.

Also, disclosed herein is a method for promoting recovery from a stroke induced loss of motor function in a subject comprising placing at least one recording electrode in electrical communication in a perilesional region of the subject; placing at least one stimulation electrode in electrical communication with the brain of the subject; recording low frequency oscillations from the perilesional region of the subject; and delivering current stimulation to the brain of the subject.

Further disclosed herein is a neurostimulation system for improving recovery in a subject with a brain lesion, the neurostimulation system comprising: an electrode; and an operations system, wherein the electrode and operations system are constructed and arranged to deliver current to the brain of the subject in response to low frequency oscillations in the brain.

In certain aspects, the neurostimulation system, further comprises at least one electromyography electrode, constructed and arranged to record muscle movement of the subject. According to exemplary embodiments, the operations system delivers current to the brain of the subject upon co-occurrence of perilesional low frequency oscillations and subject muscle movement.

DETAILED DESCRIPTION

Figure 1D:
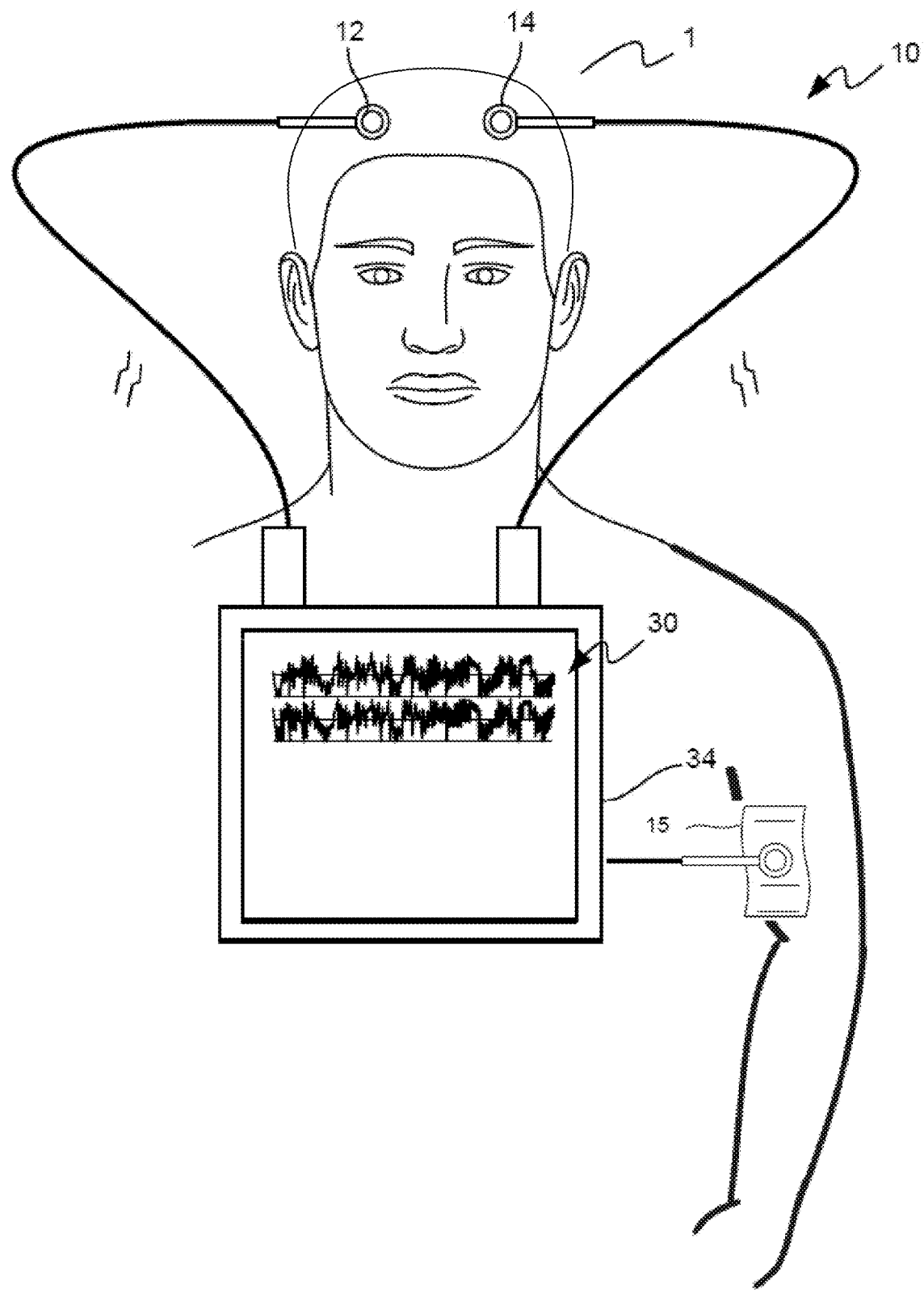
FIG. 1 shows schematic representations of the systems and methods according to certain embodiments.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the term "subject" refers to the target of administration, e.g., an animal Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed systems and methods, the subject has been diagnosed with a need for treatment of one or more stroke related loss of motor function prior to the treatment step.

Certain implementations disclosed and contemplated herein relate to neurostimulation devices—and related systems and methods—that can detect low frequency oscillations in stroke patients and utilize that information to make treatment decisions. Further embodiments relate to neurostimulation devices, systems, and methods that can augment the low frequency oscillations (LFOs) by applying direct current to the patient, including, in some such embodiments, real-time application of direct current and/or responsive application of direct current in response to detection of predetermined oscillation levels. Such responsive embodiments could be responsive to patient brain waves and requests for task-directed movement.

In certain aspects, disclosed are a method, system and associated devices for improving the motor function of a subject having suffered a loss of motor function as the result of a stroke. In certain implementations, the method involves recording activity from perilesional regions of the subject's brain. Through the recording of perilesional activity, the method seeks to detect LFOs, which have been surprisingly found to correspond to motor task learning/relearning during recovery. In certain implementations, the method further involves the application of discrete pulses of CS to perilesional regions which has been surprisingly found to potentiate motor task related LFOs, which thereby enhances relearning and recovery of motor function.

In certain embodiments, the application of CS is triggered by the detection of perilesional LFOs. In certain alternative embodiments, the application of CS is triggered by the onset of the subject's attempt to perform a motor task. In these embodiments, the CS may be delivered concurrently with the onset of the task attempt or immediately preceding task attempt. In still further alternative embodiments, CS is triggered by the co-occurrence of LFO detection and task attempt.

Disclosed herein is a neurostimulation system for promoting subject recovery from a brain lesion that includes at least one electrode, and an operations system in electrical communication with at least one electrode, wherein the at least one electrode is constructed and arranged to apply current across the brain of the subject and to record low frequency oscillations from a perilesional region of the subject.

In certain aspects, the at least one electrode is a single electrode capable of both recording LFOs and delivering current to the subject. In further embodiments, the at least one electrode comprises at least one recording electrode and at least one stimulation electrode for delivery of current to the brain of the subject. In certain aspects, electrodes are cranial screws. In further embodiments, the electrodes are one or more subdural electrodes. In exemplary embodiments, the one or more subdural electrodes comprise a plurality of electrodes arranged in an array. In these embodiments, the electrodes may be placed on a perilesional region of the motor cortex. According to still further embodiments, the one or more electrodes are depth electrodes, placed in one or more subcortical structure.

In certain aspects, the current delivered by the system is direct current stimulation. According to certain alternative embodiments, the current stimulation delivered by the system is alternating current stimulation. In exemplary aspects of these embodiments, the operations system delivers alternating current stimulation in phase with the recorded low frequency oscillations. Further alternative embodiments, the ACS is delivered at a predetermined frequency. For example, in certain embodiments, the ACS is delivered at between about 0.1 to about 1000 Hz. In further embodiments, is delivered at between about 0.1 to about 4 Hz. In certain embodiments, the frequencies may be dynamically altered during the course of stimulation.

In certain aspects, the operations system is constructed and arranged to apply current in response to recorded electrical activity. According to alternative embodiments, the operations system is constructed and arranged to deliver current in response to subject movement.

Disclosed herein is a method for promoting recovery from a stroke induced loss of motor function in a subject comprising placing at least one recording electrode in electrical communication in a perilesional region of the subject; placing at least one stimulation electrode in electrical communication with the brain of the subject; recording low frequency oscillations from the perilesional region of the subject; and delivering current stimulation to the brain of the subject.

In certain aspects of the instantly disclosed method, the current stimulation is delivered by direct current stimulation.

According to certain alternative embodiments, of the disclosed method, current stimulation is delivered by alternating current stimulation, delivered in phase with the low frequency oscillations. According to these embodiments, the LFO recorded at the perilesional site is used to determine the stimulation parameters of the alternating current stimulation. That is, the wave form and frequency of the alternating current stimulation is calculated to match the recorded LFO. In exemplary embodiments, the onset of the alternating current stimulation is concurrent with a peak of a low frequency oscillation waveform.

According to further aspects, the method further comprises the step of instructing the subject to perform a predefined motor task. In these embodiments, the motor task is predetermined to target the motor function effected by the brain lesion. In certain embodiments, current stimulation is delivered concurrently with subject's performance of the motor task. In further embodiments, the onset of the current stimulation immediately precedes instruction to the subject to perform the motor task. In exemplary embodiments, the onset of current stimulation is about 500 ms prior to the motor task and continues through the completion of the motor task. According to certain alternative embodiments, the current stimulation is triggered by the co-occurrence of motor task performance and LFO detection.

In certain aspects, the disclosed method is performed during sleep of the subject. In such embodiments, application of CS or ACS (0.1-1000 Hz) during sleep potentiate LFOs associated with recovery of motor function. In certain exemplary embodiments, during sleep following a training session, LFOs associated with improvement-related plasticity can be further potentiated by application of CS or ACS.

In certain aspects, current stimulation is delivered to the perilesional region of the subjects brain. According to certain alternative embodiments, the current is also delivered to one or more subcortical structures. Exemplary structures include but are not limited to the striatum, motor thalamus, red nucleus, cerebellum, red nucleus and/or spinal cord structures and peripheral structures. According to certain exemplary embodiments, alternating current stimulation is delivered to these structures, in phase with LFO recorded in the perilesional region during motor task performance.

Further disclosed herein is a neurostimulation system for improving recovery in a subject with a brain lesion, the neurostimulation system comprising: an electrode; and an operations system, wherein the electrode and operations system are constructed and arranged to deliver current to the brain of the subject in response to low frequency oscillations in the brain.

In certain aspects, the neurostimulation system, further comprises at least one electromyography electrode, constructed and arranged to record muscle movement of the subject. According to exemplary embodiments, the operations system delivers current to the brain of the subject upon co-occurrence of perilesional low frequency oscillations and subject muscle movement.

Turning now to the figures, FIG. 1A depicts an overview of the closed-loop stimulation (CLS) system 10 according to one implementation. In these implementations, the CLS system 10 is triggered by task-related low-frequency oscillation (LFO) power. As is shown in FIG. 1A, the system 10 has at least one electrode 12, 14, here a delivery electrode 12 and at least one recording electrode 14. In these implementations, the screws 12, 14 are implanted or otherwise disposed on the skull 16 of the patient. In various implementations, these electrodes 12, 14 are cranial screws, though other kinds of electrical, implantable devices are also contemplated.

As shown in FIGS. 1B-C, in certain implementations, the distal end 12A of an electrode or screw can be disposed partially through the skull bone 18 (FIG. 1B), such that there is no penetration of the cranial vault. In alternate implementations, the distal end 12E can be disposed through the skull bone 18 so as to be in the epidural space (FIG. 1C). It is understood that in further implementations the screws may be placed subdurally or even intracortically, such as disposing the distal end such that it is touching and/or penetrating the cortex itself. It is understood that further implementations and combinations of these placements are possible, such that the distal ends are disposed so as to best deliver and/or receive current in the desired application or implementation.

Returning to FIG. 1A, in various implementations, the various delivery electrodes 12A, 12B can be disposed perilesionally, adjacent to, or proximal to the lesion 20. Other delivery screws 12C can be disposed apart from the lesion 20, such as near the frontal cortex. The recording screw 14 can also be disposed perilesionally, adjacent to, or proximal to the lesion 20. In various implementations, both the delivery screws 12A, 12B, 12C and recording screws 14 are in electrical communication with an external operations system (generally at 24). The operations system 24 is configured to deliver current stimulation (CS) by way of the delivery screws (as is shown in relation to screw 12A) and receive low frequency oscillation signals (LFO) from the recording screw 14. In an alternate embodiment, both recording and stimulation can be achieved through the same cranial screws.

In various implementations, the operations system 24 is a closed-loop and is configured to apply CS and record LFO on a time-scale and compare it with recorded patient movement. In certain implementations, the movement of an area of the body will trigger LFO. In certain implementations, in response to observed LFO (reference arrow A), the operations system 24 can apply (reference arrow B) direct-current stimulation (reference arrow C) to the subject's brain through the delivery screws 12A, 12B.

In use, and as is shown in FIG. 1D, in an exemplary implementation, electrodes 12, 14 are affixed to or otherwise disposed within the head of the patient 1. In these implementations, these electrodes are in electrical communication with an operations system 30 via wires or other connections. In various implementations, the operations system can be a desktop or handheld device constructed and arranged to send and receive electrical signals and/or currents. In various implementations, the operations system 34 has a processor, and can be any computer or processor known to those skilled in the art. In one embodiment, the operations system 34 includes software, which may be hosted in at least one or more computer servers, and can further comprise any type of known server, processor, or computer, any of which can run on a variety of platforms.

In accordance with one implementation, the operations system 34 has a central processing unit ("CPU") and main memory, an input/output interface for communicating with various databases, files, programs, and networks (such as the Internet, for example), and one or more storage devices. The storage devices may be disk drive devices, CD ROM devices, or the cloud. The operations system 30 may also have an interface, including, for example, a monitor or other screen device and an input device, such as a keyboard, a mouse, a touchpad, or any other such known input device. Other embodiments include corresponding computer systems, apparatus, and computer programs recorded on one or more computer storage devices, each configured to perform the actions of the methods.

It is further understood that in certain implementations, such as that of FIG. 1D, the system 10 can also include one or more peripheral monitoring devices or systems 15. In various implementations, these peripheral monitoring systems 15 can be electrodiagnostic devices or systems such as electromyographs 15 or other known diagnostic or monitoring devices. It is further understood that the peripheral monitoring system 15 is not essential for operation of the system 10.

Figure 1E:
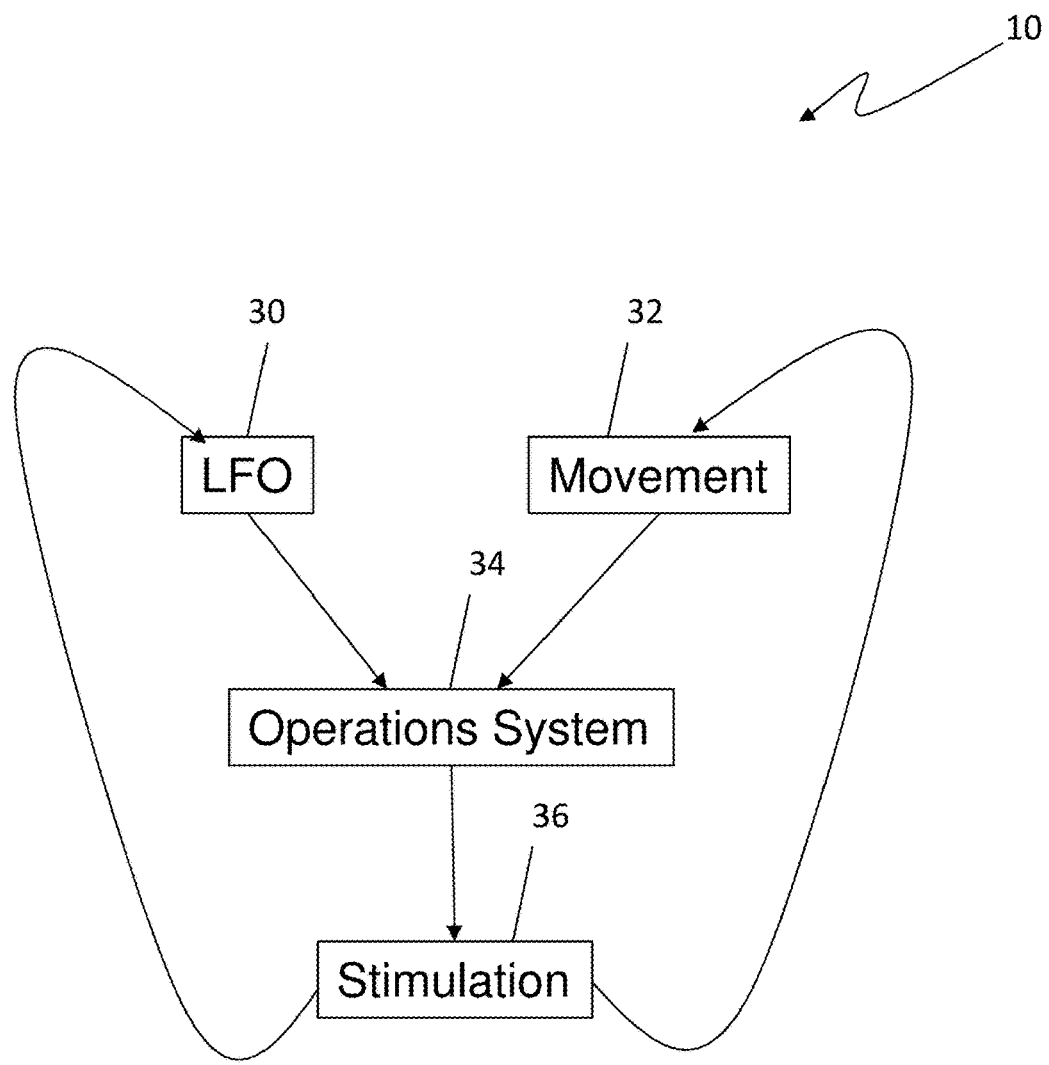
Figure 1F:
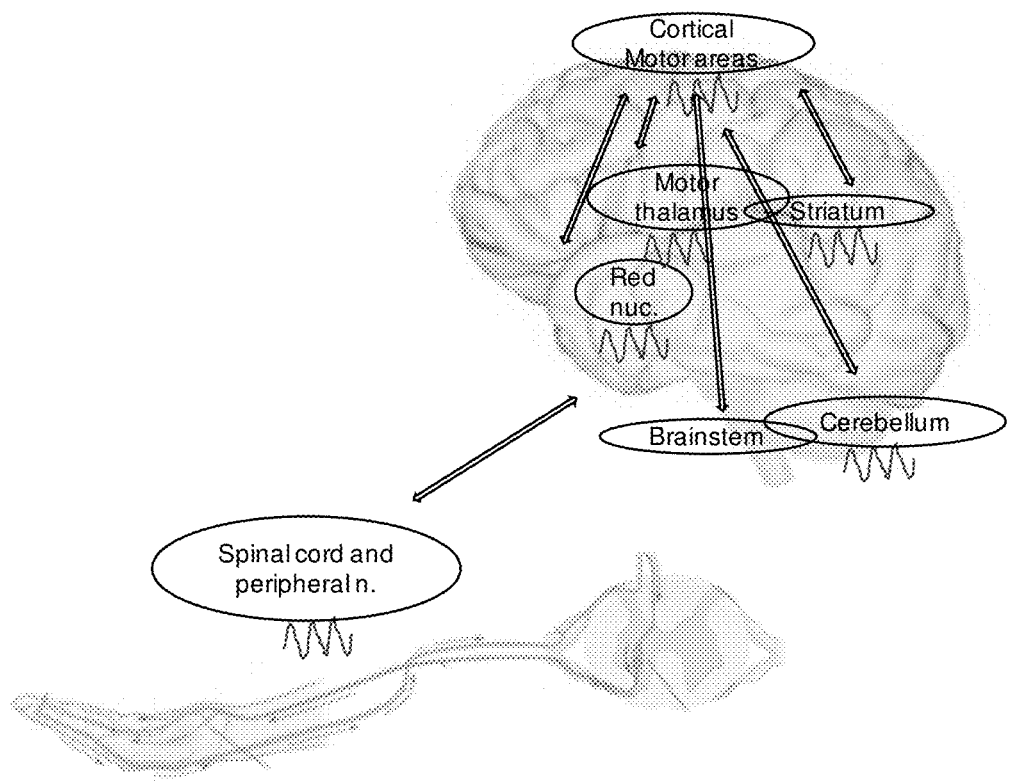

It is understood that in use according to various implementations, the system and various methods can be executed via a number of optional steps. In one step, and as shown in FIG. 1E, LFO from the recording electrode (shown as box 30 in FIG. 1E) and/or movement—such as electromyography (EMG) from the peripheral monitoring system 15 (box 32) can be recorded by the operations system (box 34), which can also apply CSelectrical stimulation (box 36). It is understood that in certain implementations, another step involves the application of current (box 36). In certain implementations, the application of current (box 36) can be initiated by detection of LFO (box 30). In further implementations, the application of current (box 36) can be initiated by movement of the subject (box 32). In further implementations, these steps can be performed concurrently, consecutively or independently. In embodiments in which CS is triggered independently, a healthcare provider, such as a physical therapist, can trigger the application of CS as in conjunction with instructing the subject to perform a therapy related motor task. It is further understood that the onset of stimulation can include "pre-movement" stimulation, which can be titrated between seconds to milliseconds prior to movement. Alternate embodiments use different neural signatures for CLS. For example, a combination of LFO with EMG signals in proximal arm muscles (e.g. deltoid, trapezius or latisssimus dorsi) can trigger CS. In this implementation, the LFO and the EMG can be used equally to trigger CS. In further implementations, the EMG signal from proximal muscles could also be used alone to trigger the "pre-movement" CS. In yet further embodiments, movement is detected by sensors placed on the body of the subject. For example, one or more accelerometers can be placed on the limbs of the subject and signals from the one or more accelerometers can be used to trigger CS.

EXPERIMENTAL EXAMPLES

The following examples are put forth so as to provide those of ordinary skill in the art with a complete disclosure and description of how the articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

It is commonly hypothesized that restoration of normal neural dynamics in the injured brain can improve function. However, we lack a precise neurophysiological framework for such an approach. Here we show that low-frequency oscillatory (LFO) dynamics play a critical role in the execution of skilled behaviors in both the intact and injured brain. We chronically recorded local field potentials and spiking during motor training in both healthy and post-stroke rats. Interestingly, we found that task-related LFOs emerged with skilled performance under both conditions and were a robust predictor of recovery. We further hypothesized that boosting LFOs might improve function in animals with persistent deficits. Strikingly, we found that direct current stimulation could boost LFOs, and when applied in a novel, task-dependent manner, significantly improved function in those with chronic deficits. Together, our results demonstrate that LFOs are essential for skilled controlled and represent a novel target for modulation after injury.

We first assessed the dominant LFP oscillatory dynamics associated with motor reaching in healthy animals, to confirm whether low-frequency oscillations, as identified in primates during motor actions, were similarly important in rodents. Rats were implanted with microwire arrays within motor cortex (M1) prior to learning a skilled forelimb reach task. This task required animals to reach out of a box, grasp a pellet placed on a small pedestal, and retract its arm back into the cage (FIG. 2A). This motor behavior requires significant dexterity of the distal forelimb and is dependent on M1 Animals were trained over multiple days using an automated reach-box that synced behavioral and electrophysiological data.

The dominant neural oscillation associated with the skilled motor reach task, i.e. averaged across all trials in all animals, occurred in the lowest-frequency bands (FIG. 2B). In addition to increased power, we also found significant task-related phase-locking of these lower-frequencies in association with the motor action. We next performed a t-test comparing changes in phase-locking at frequencies ranging from 1.5—60 Hz (a total of 117 frequencies), across a time-window from −10 ms to 500 ms compared to a pre-reach baseline period to assess which frequencies showed the largest evoked phase-locking related to reach-onset. We found that frequencies <8 and those between 11-13 Hz showed significant task-related phase-locking (paired t-test, $p<0.05$, FWE-corrected for 117 frequencies). However, frequencies <4 Hz showed the most significant phase-locking.

Based on these results, we focused on the plasticity of low-frequency oscillations, i.e. <4 Hz, in motor leaning and recovery after stroke.

Interestingly, we found a clear evolution in LFOs with learning (FIG. 2C). As animals learned the task, the skilled motor action became temporally bound together and independent sub-movements became more phase-locked to the LFO (FIG. 2C-D), resulting in a significant increase in both task-related LFO power and LFO phase-locking to the motor actions; for this and all future calculations of LFO, unless otherwise indicated, we used frequencies <4 Hz (FIG. 2E, n=64 electrodes from 4 animals, * above is paired t-test $p<0.05$, FDR corrected). Averaged across a relevant reach-related time-window, i.e. −10 to 500 ms from reach-onset, we found on average an increase of 356±105% ($p<0.01$, paired t-test, n=64) in power and a 62±7.5% increase in phase-locking ($p<0.001$, paired t-test, n=64) with stable skill acquisition. It is important to note that trials were only included if the animal successfully reached and touched the pellet. We again performed a t-test comparing changes in phase-locking at frequencies from 1.5-60 Hz to assess which frequencies showed the largest change in phase-locking. Notably, we found that only frequencies <12 Hz showed an increase in phase-locking with learning; the largest changes occurred at frequencies <5 Hz; paired t-test, $p<0.05$, FWE-corrected).

It has been theorized that LFOs bind M1 microcircuits, including spiking activity of individual neurons, with mesoscale cortical dynamics (Bansal et al., 2011; Hall et al., 2014). We performed two types of analysis to probe this. We first assessed spike-field coherence (SFC), a measure of the relationship between spiking activity and the phase of oscillations at a specified frequency (Bokil et al., 2010; Buzsáki et al., 2012; Fries et al., 2001). We found many neurons demonstrated strong SFC to LFOs during the reach task, suggesting these slow oscillations play an important role in organizing M1 microcircuits (FIG. 2F). The strength of this coupling increased by 38±15%, as measured across the same time-window described above, when comparing SFC of neurons recorded on the first vs. the last day of skilled motor training (FIG. 2F n=62 from early and 64 from late sessions, 2-sample t-test, $p<0.001$).

To examine how motor training affects mesoscale LFO dynamics within M1, we used principle-components-analysis (PCA) to quantify dynamical patterns across M1 during task execution, using previously described techniques. Specifically, we plotted the trajectory of the first 3 principle-components, calculated across M1 channels, during the motor reach task. We found a striking increase in the stereotypy of these LFO neural trajectories with learning (FIG. 2G; shows examples of simultaneously plotted PC and movement trajectories from early and late trials in one animal). In order to quantify this effect across animals, we calculated the inter-trial correlation of the PC trajectory space across trials. The emergence of stereotyped mesoscale dynamical patterns occurred primarily in lower-frequency bands (maximal stereotypy increase with learning occurs at lower frequencies <5 Hz). FIG. 2G was calculated using the average Fisher-Z transformed inter-trial correlation value, n=4900 trials/frequency for early and late blocks, collected from 4 animals using 50 trials for each block. Stars indicate frequencies that show a significant increase in inter-trial correlation of the PC trajectory, using a $p<0.001$ threshold, FWE-corrected for 18 comparisons. Together, our results indicated that with skilled motor learning, the strength and phase-locking of LFOs increased and served to dynamically modulate the spiking activity of M1 neurons.

To probe the causal role of these cortical oscillations in the production of skilled motor behaviors, we used a photothrombotic stroke model to induce focal M1 lesions in well-trained animals Immediately after the stroke, 16 or 32-channel micro-wire arrays were implanted in perilesional cortex anterior to the lesion, as described previously (Gulati et al., 2015) (FIG. 3A). Animals were given one week to recover from the stroke injury/electrode placement, after which they underwent motor training sessions on the same task for an additional 5-8 days to assess the relationship between motor recovery and modulation of task-related LFOs in perilesional cortex (FIG. 3B-C). Injury resulted in impaired motor performance; there was a drop in accuracy from 87±5% pre-lesion to 24±11% after the stroke, p<0.01. As expected, animals demonstrated an improvement in motor function over the course of training (FIG. 3B). The mean accuracy increased from 36±12% accuracy (average of first two sessions) to 65.4±7% (average of last two behavioral sessions), p<0.05, paired t-test.

Impaired motor performance after the injury was associated with diminished LFOs in perilesional cortex and recovery of motor function in each animal was linked with a strong increase in these LFOs (FIG. 3C). Over the course of rehabilitation training, animals demonstrated a 584±157% increase in LFO power (FIG. 3D, paired t-test of % increase in Z-scored power across channels averaged across reach-related time-window, n=176 channels from 6 animals, p<0.001). This increase in LFO power was a highly significant predictor of motor recovery. We specifically compared the mean LFO power change for a session (i.e. relative to the first session post-stroke across channels in each animal) and the average accuracy change (i.e. relative to the first session post-stroke; FIG. 3E, r=0.55, p<0.001). Consistent with the notion that LFOs dynamically organize motor cortical areas, we also found that recovery of function was associated with increased phase-locking of perilesional spiking activity with the low frequency oscillations (FIG. 3F example animal showing SFC for all units at two time points, FIG. 3G, n=127 units from early sessions, and 169 units from late sessions, p<0.001 2-sample t-test averaged across reach-related time-window). As with healthy animals, there was also a significant increase in task-related LFO phase-locking of 27±3.7%, p<0.001.

We next examined whether electrical stimulation targeted to LFOs might improve motor function after stroke. We analyzed the effects of CS on M1 low-frequency oscillatory activity during ketamine anesthesia; neural recordings during anesthesia are of substantially greater quality and can allow us to easily monitor spiking and LFP during stimulation. After anesthetic induction, we implanted epidural electrodes for stimulation and M1 microwire electrodes to measure neural activity (FIG. 4a). Baseline spiking/LFP activity was recorded for 15 minutes; this was followed by recordings during the application of a 1-5 minute long CS via the cranial screw adjacent to the implanted electrodes. Interestingly, we found that CS could effectively modulate ongoing LFO dynamics during ketamine anesthesia (FIG. 4b-c). More specifically, CS significantly increased LFP power in the lower frequencies, (FIG. 4b, example animal, p<0.05 across 10 animals comparing 1.5 to 4 Hz power pre-versus during stimulation). CS also increased neural SFC (FIG. 4c, p<0.01, n=51 neurons, from 1.5-4 Hz); SFC analyses controlled for any firing rate changes. These results indicate that CS can directly boost LFOs, i.e. a concomitant increase in both LFP power and the phase coupling of spiking activity.

Having found that a low-strength electric field CS could modulate low-frequency oscillations, we next performed experiments to assess whether short pulse of CS (<5 seconds in duration) applied directly during the reaching behaviors could improve motor function after stroke. Importantly, we avoided the significantly longer-duration pulses (e.g. continuous for ≥10 minutes) that are known to induce long-lasting changes in excitability; we wanted to specifically assess whether transient on-demand stimulation could induce behavioral improvements. For these experiments, animals underwent either a photothrombotic (n=4) or distal-MCA (n=3) stroke induction and were implanted with cranial screws for stimulation both anterior and posterior to the injury site (FIG. 5a). Animals then underwent motor training for days to weeks until their level of performance plateaued; CS stimulation was then tested.

Stimulation experiments occurred between 20 and 150 days after the stroke across animals, with no clear relationship between time after stroke and efficacy of stimulation. We compared the effects of stimulation with a "no-stimulation" and a "sham-stimulation" condition (FIG. 5b). Importantly, we clearly found that stimulation effects were truly "on-demand" and did not persist across blocks. Thus, for each daily session we could test all three conditions (i.e. blocks of trials of no stimulation, sham, stimulation). The order of these blocks was pseudo-randomized across days in every animal, and across sessions; we did not find that order of block affected results. We calculated the percent improvement in accuracy for each daily stimulation and sham condition relative to the no-stimulation condition for that day. Animals showed an improvement of 73±12% in accuracy following stimulation (one-sample t-test, t(6)=6, p<0.001) and a non-significant change of −4±5% in the sham stimulation group (one-sample t-test, t( )−0.77, p>0.05). There was also a significant difference in the observed behavioral effects between the stim and sham conditions (paired-t test, t=4.9, p<0.01). We observed improvements in performance in both stroke models with no significant differences in the effects observed by stroke model type (F(1,5)=1.5, p<0.05). While the above experiments were conducted using cathodal stimulation, we found similar effects using anodal stimulation condition (anodal-stimulation showed an improvement of 60±12% (one-sample t-test, t(4)=4.9, p<0.01, n=5 animals). There was no difference between anodal and cathodal stimulation groups in the effect of stimulation on motor improvement (ANOVA, F(1,10)=1.35, p>0.05).

The results above used relatively long duration pulses relative to the duration of a typical reach-to-grasp movement (i.e. ~700 ms). We also tested whether 1 second long stimulation pulses could allow us to more precisely determine the temporal relationship between electrical stimulation and the neural processes underlying reach control after stroke. For each reach trial, we randomly varied the precise timing of stimulation onset relative to when the door opened as a 'Go' cue (FIG. 6a). Importantly, the only parameter varied was the timing of the stimulation onset relative to this cue. Next, we calculated the ΔT between stimulation onset and the actual reach onset for each trial; this allowed us to account for variations in the reaction time. We then calculated the % accuracy for all trials at a particular ΔT by binning all trials in a window of ±100 ms around that time-point. Across 4 animals we observed a significant improvement in accuracy only when ΔT occurred between 500-400 ms from the reach (FIG. 6b, p<0.05, bootstrapped). Given that we used 1 second pulses, this indicated that stimulation pulses that started prior to reach onset and lasted through the duration of the reach were the most effective. Interestingly, this timeframe may be related to the expected period for task related LFOs. As a possible metric for comparison, we plotted the mean task evoked LFO (data from FIG. 3). Together, our data suggests that stimulation pulses that maximally overlapped with the neural dynamics prior to and during the reach were the most effective at improving function.

It is important to note that electrical stimulation can have differential effects related to the onset/offset of stimulation as well as during the "steady-state" or the DC field effect. This may explain the significant worsening that was observed for stimuli that started 0.975 seconds prior to reach onset (FIG. 6b green star; i.e. the offset was exactly at the time of reach onset). Perhaps also consistent with this interpretation is the finding that pulses that started immediately prior (i.e. <500 ms) to movement onset or during the movement did not result in consistent beneficial effects. Together with the results from FIG. 6, our results indicate that pulses that start at least 500 ms prior to reach onset and last through the reach are consistently able to improve reaching behaviors.

We next assessed whether our observed phenomena in rodent models could also apply to human stroke. In order to assess this, we reanalyzed human ECoG (ElectroCortiocoGraphy) data collected from human subjects undergoing invasive epilepsy monitoring. All subjects underwent invasive ECoG monitoring to identify seizure foci. Physiological data were recorded during a center-out reach task in which subjects were instructed to wait for a start cue and then reach as fast as possible to a target (FIG. 8a). Two of these patients had intact sensorimotor cortices (hereafter Intact Subjects or IS1/IS2) and the third had a cortical stroke particularly affecting the arm and hand motor areas (hereafter Stroke Subject or SS) (FIG. 8b). The stroke subject had persistent motor deficits involving arm and hand movements (Fugl-Meyer upper-limb score of 35). He also showed impairments in speed of execution. Reaction time from the "Go" cue to movement onset (i.e. rise in mean EMG activity) was slower for the affected versus unaffected arm (mean reaction time of 635±40 and 365±18 ms, respectively, P<0.001, unpaired t-test). Similarly, the reach time from movement onset to target acquisition was longer for the affected arm (mean reach time of 1266±58 ms vs. 856±26 ms, P<0.001, unpaired t-test).

With respect to the EcoG recordings for the two intact subjects, we found evidence for robust task-related LFOs centered around sensorimotor cortex (FIG. 6c). The time course and pattern of this activity appeared to closely resemble that observed in rodents. In the stroke subject, however, there was a striking loss of this sensorimotor reach-related low-frequency activity (FIG. 8c-e). The mean normalized LFO activity for sensorimotor electrodes (from −300 ms to +300 ms) was significantly positive for the two non-stroke subjects (Subject 1, normalized mean activity 0.55±0.2, n=18 SM electrodes, t(17)=7.2, p<0.001) and 0.93±0.25 in the second subject, (n=16 SM electrodes, t(15)=5.5, p<0.001), while the stroke subject showed no significant increase activity (−0.12±0.1, n=91 SM electrodes, t(90)=−1, p>0.05). There was a highly significant difference in task-related low frequency power between the stroke subject and the two healthy subjects, (F=9.8; p<0.001; post-hoc p<0.01, Bonferonni corrected, comparing stroke subject to each of the healthy subjects; post-hoc tests confirmed with bootstrapping implemented within SPSS). There was no difference between the two healthy subjects (p>0.05). Importantly, prior analyses of the data from the stroke subject demonstrated intact high-gamma activity in much of the brain, including sensorimotor cortex, despite motor deficitsFIG.FIG.. High-gamma is widely thought to represent local spiking activity. These results suggest that low-frequency oscillatory activity is a common electrophysiological signature of healthy motor circuit function across both rats and humans, and in both species stroke appear to disrupt this task-related physiological marker even in brain areas demonstrating reach-related spiking activity (i.e task related spiking modulation in rats and high-gamma activity in the ECoG recordings).

Figure Legends

Figure 2:
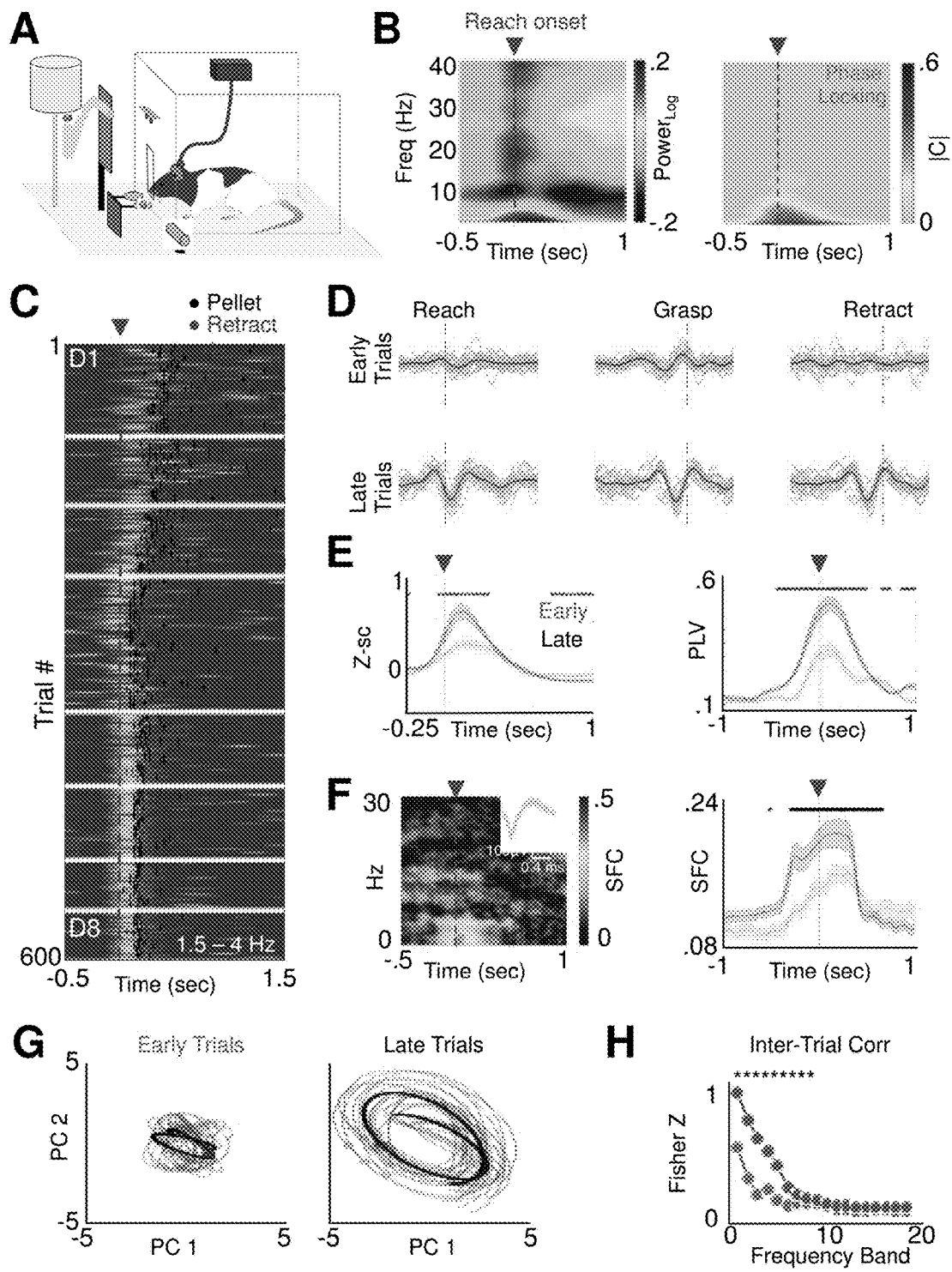
FIG. 2 shows data indicating changes in Low-Frequency Oscillatory (LFO) dynamics during motor learning.

FIG. 2: Changes in Low-Frequency Oscillatory (LFO) Dynamics During Motor Learning. a. Neurophysiological signals were recorded as rats learned a skilled forelimb reach task. b. Average task-evoked power and inter-trial phase-locking (n=4 animals) Red arrow indicates reach onset time in this and all subsequent panels. To quantify significant deflections during the reach period, a paired t-test was performed for each time-frequency point, compared to the mean power for that frequency during a base-line period (−3 to −2 s prior to reach), across trials, followed by FDR-correction (p<0.05). Green shading indicates points that did not reach significance. c. Evolution of LFO power in a single M1 LFP channel over time. White bars separate days (e.g. D1-D8). Z-sc=Z-scored. d. Comparison of LFOs for each submovement for early (Trials #1-25) and late trials (Trials #575-600). Late trials illustrated temporal binding and increased LFO power. e. Significantly increased power (Z-scored) and phase-locking (PLV) from early (first 50) to late (last 50) trials with learning (n=64 recording channels across 4 animals). Stars above indicate specific time points that were significant at a p<0.05, using FDR-corrected paired t-test. f. Example neural spike-field coherence (SFC). Comparison of mean SFC for early and late trials (n=3 animals, 126 neurons), significance assessed using 2-sample t-test. (stars indicate time-points after FDR correction, p<0.05) g. Comparison of LFO PCA trajectories for early and late trials from one animal. Changes in trajectory stereotypy were quantified by calculating the inter-trial trajectory correlation (Fisher-Z transformed) from the first 50 and last 50 trials in each animal, across different 2-Hz band-pass filters (i.e. from 1-3; 2-4; etc.). Stars indicate frequency bands that also show an overall increase (p<0.001, FWE-corrected across 18 frequency bands).

Figure 3:
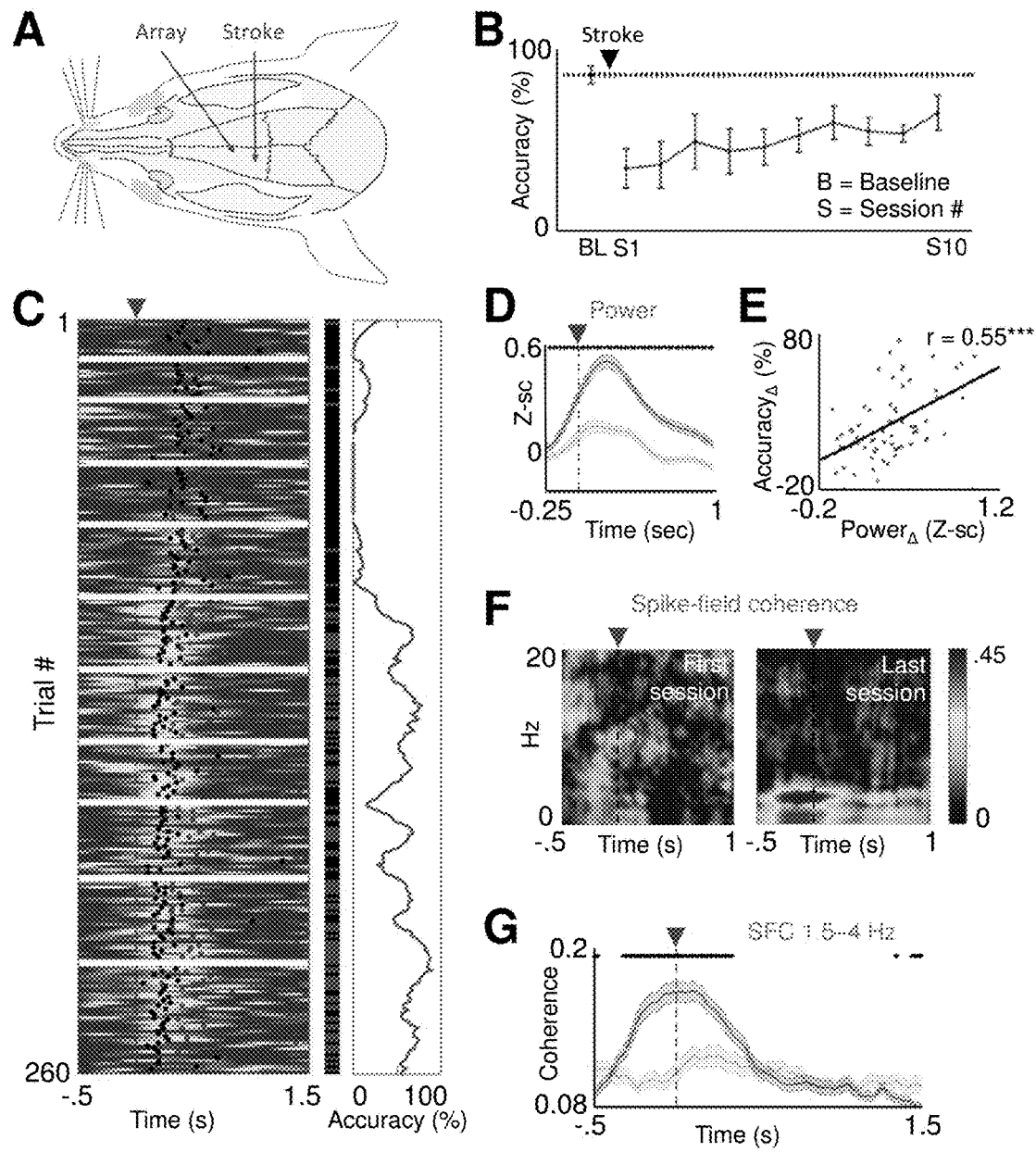
FIG. 3 shows data showing LFO dynamics during motor recovery after stroke, according to certain embodiments.

FIG. 3: LFO Dynamics During Motor Recovery After Stroke. a. Focal photothrombotic stroke was performed to induce cortical lesions, followed by implantation of a 16 or 32 channel electrode array in the anterior perilesional cortex. b. Changes in reaching behavior with time (S1 was 1 week post stroke for all). Each animal typically attempted 50-75 trials/day. c. Example of change in LFO power with motor recovery. All shown trials involved the animal at least reaching and knocking off the pellet. d. Across animals, there was a significant increase in tasked-related LFO power with time (n=176 channels from 6 animals, paired t-test comparing early and late trials as described in FIG. 2e, * above is 2-sample t-test, p<0.05, FDR-corrected for multiple comparisons across time-points). e. LFO power was a significant predictor of recovery. f. Example change in neural spike-field coherence with recovery (one neuron from first and last sessions). g. Across neurons/animals, we found a significant increase in SFC with recovery (n=296 units). * above is 2-sample t-test, p<0.05, FDR-corrected for multiple comparisons across time-points.

Figure 4:
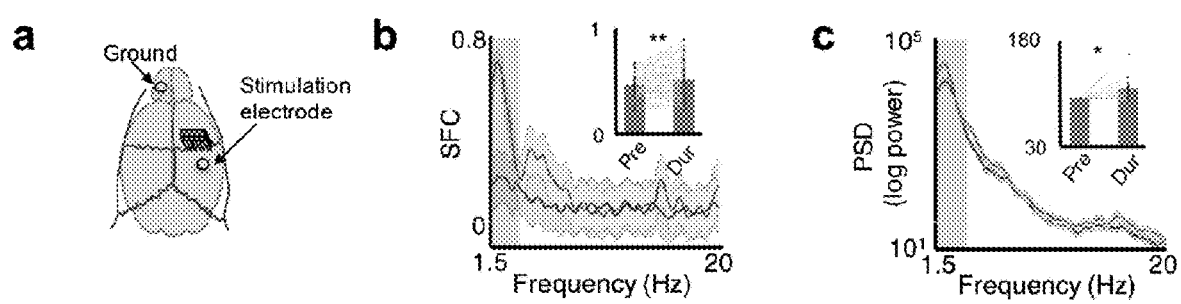
FIG. 4 shows modulation of LFO dynamics using direct current stimulation (CS), according to certain embodiments.

FIG. 4: Modulation of LFO Dynamics Using Direct Current Stimulation (DCS). a. Acute experiments under ketamine anesthesia. Stimulation was performed using a screw implanted posterior to the craniotomy with the ground screw implanted in the contralateral hemisphere. b. Example showing an increase in neural SFC during DCS. c. Example of changes in LFO SFC during DCS (n=7 animals). 46% of neurons showed an increase in excitability (Rate+), 23% of neurons showed a decrease in excitability (Rate−), and 31% of neurons were not modulated ($Rate_0$). Only those neurons that showed a change in excitability showed a modulation in spike-field coherence (F=13.1, * p<0.001).

Figure 5:
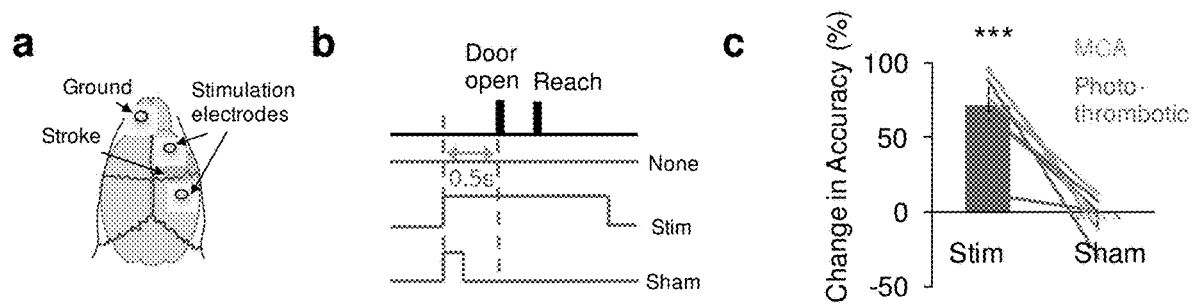
FIG. 5 shows data showing task-dependent CS improves motor function, according to certain embodiments.

FIG. 5: Task-dependent DCS Improves Motor Function. a. Skull-screws for stimulation were implanted both anterior and posterior to the stroke lesion. The ground screw was implanted in the contralateral hemisphere. b. Sessions were pseudo-randomized each day into a block of 30-35 trials. In each block of trials, animals were administered either DC stimulation, a "sham-stim" control (stimulation turned on for only 200 ms), or no stimulation. d. DCS significantly improved reach accuracy after stroke (n=7 animals) There were no significant differences observed in the percent improvement in MCA vs. photothrombotic stroke models.

Figure 6:
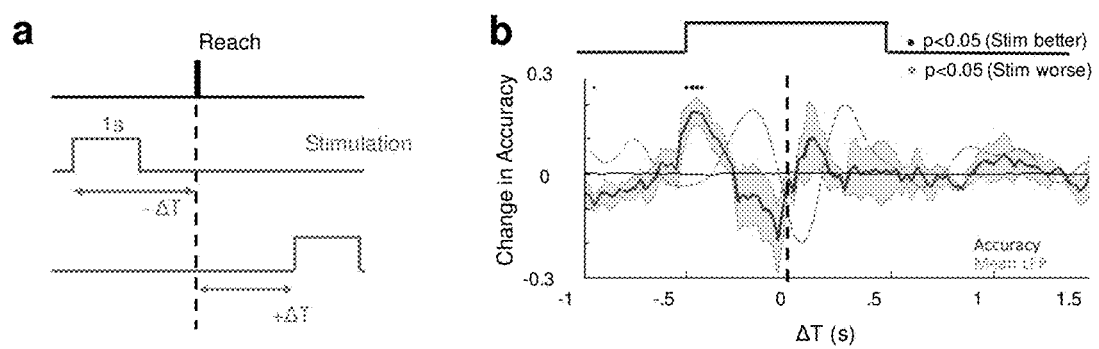
FIG. 6 shows data indicating that precisely time-locked stimulation improves motor function.
Figure 7:
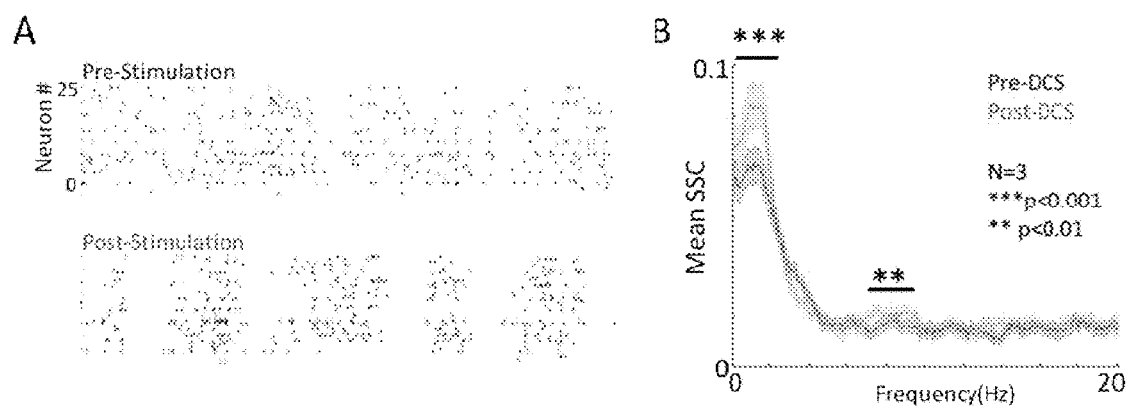
FIG. 7 shows data showing enhancement of phase-locking with anodal TCS during sleep

FIG. 6: Precisely Time-Locked Stimulation Improves Motor Function. a. Stimulation was delivered on every trial pseudo-randomly timed to occur either before, during or after the trial began. The stimulation pulse lasted for only 1 second. ΔT was calculated between the stimulation onset and the actual reach-onset for every trial. b. For each animal, we binned and calculated the percentage accuracy at each ΔT (binning occurred using a window of ±100 ms, with a moving window of 25 ms between time points). We calculated, across animals, the accuracy difference at different ΔTs (accuracy at each ΔT subtracted by the mean accuracy across all trials and stimulation times for that animal) We also found certain time points in which stim was associated with worse performance relative to base-line (denoted in green). Significant improvements denoted by blue diamonds. The corresponding stimulation pulse is denoted in blue above the image. Grey line shows the mean 1.5-4 Hz LFP from healthy animals FIG. 7: Enhancement of phase-locking with anodal TDCS during sleep. (A) Example of change in phase-locking with stimulation. Each dot is an action potential. (B) Summary of change in spike-spike coherence (SSC) with simulation. SSC is a measure of how precisely neurons co-fire. Higher values indicate more phase-locking of firing.

Figure 8:
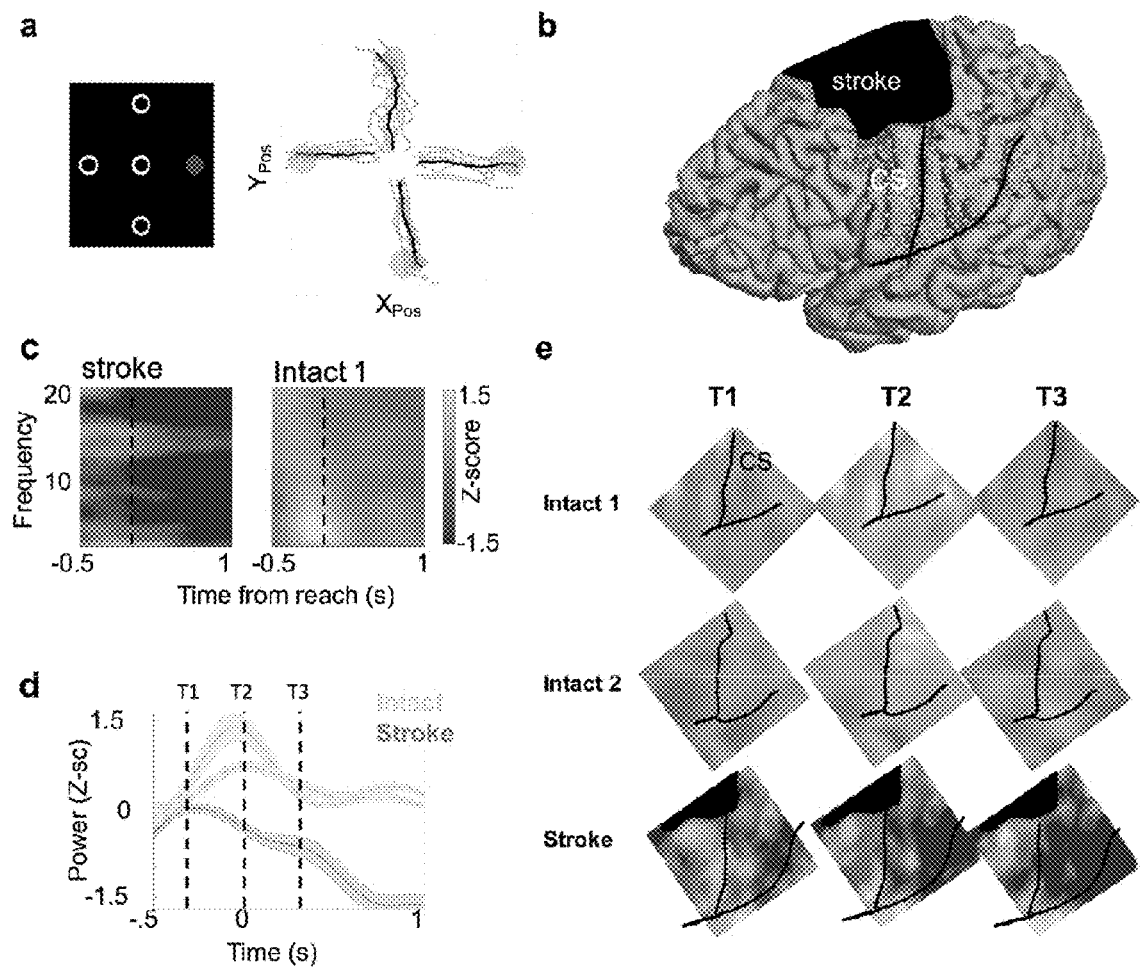
FIG. 8 shows data showing movement-related low-frequency oscillations in sensorimotor cortex in humans.

FIG. 8: Movement-Related Low-Frequency Oscillations in Sensorimotor Cortex in Humans. a. Center-out paradigm used in patients with ElectroCorticoGraphy (ECoG) recordings. In each trial, subjects were given a hold cue, followed by a "reach" cue that indicated which target to move to. Example of trajectories in the stroke patient. We recorded movement-related data from 2 healthy subjects and 1 stroke subject. Analyses were collapsed across all movement directions in each subject. b. Placement of ECoG grid in the stroke subject, and location of stroke. c. Event-related spectral power across sensorimotor electrodes from one intact subject, and the stroke subject. Power normalized to a base-line time-period for each channel (activity prior to the hold-cue). d. Temporal plot of mean low-frequency power (1.5-4 Hz) from sensorimotor electrodes in each of the 2 intact subjects and the stroke subject. e. Spatiotemporal plot at the 3 time-points indicated in panel (d), demonstrating increase in LF power along the CS (sensorimotor strip) in the two healthy subjects, and absence of this power in the stroke subject.

Methods

Animals were housed in a 12h:12h light:dark cycle. All surgical procedures were performed using sterile technique under 1-2% isoflurane or a ketamine/xylazine cocktail. Surgery involved cleaning and exposure of the skull, preparation of the skull surface (using cyanoacrylate), and then implantation of skull screws for referencing, stimulation and overall head-stage stability. Ground and reference screws were implanted posterior to lambda, with the ground screw was placed in the skull contralateral to the neural recordings, and the reference screw placed ipsi-lateral to the neural recordings. Craniotomy and durectomy were performed, followed by implantation of neural probes. In healthy animals, neural probes were centered over the forelimb area of M1(Ramanathan et al., 2006), centered at 3 mm lateral and 0.5 mm anterior from bregma.

In 10 animals, a focal photothrombotic stroke was induced over M1 centered at the above coordinates. For this procedure, after the craniotomy, rose-bengal dye was injected into the femoral vein using an intravenous catheter. After injection, the surface of the brain was illuminated with white light (KL-500) using a fiber optic cable for 20 minutes. We used a 3 mm aperture for stroke induction (centered in the M1 area based on stereotactic coordinates) and covered the remaining cortical area with a custom aluminum foil mask to prevent light penetration. After induction, a probe was implanted in the perilesional cortex (PLC) immediately anterior to with one of the outermost rows of the array implanted immediately proximal to the stroke site (Gulati et al., 2015). The craniotomy/implanted electrodes were covered with a layer of silicone (Quiksil), followed by dental cement. The postoperative recovery regimen included administration of buprenorphine at 0.02 mg/kg b.w for 2 days, and meloxicam at 0.2 mg/kg b.w., dexamethasone at 0.5 mg/kg b.w. and trimethoprim sulfadiazine at 15 mg/kg b.w. for 5 d. All animals were allowed to recover for one week prior to further behavioral training In Vivo Electrophysiology We recorded extracellular neural activity using tungsten microwire electrode arrays (MEAs, n=13 rats; Tucker-Davis Technologies). We used either 16- or 32-channel arrays (33 μm polyimide-coated tungsten microwire arrays). Arrays were lowered down to a depth of ~1300-1500 μm, and spanned an area 0.5-3 mm anterior to bregma and 2-4 mm lateral from midline in healthy animals. In stroke animals, the neural probe was placed immediately anterior to the stroke site).

Units and LFP activity were recorded using a 128-channel TDT-RZ2 system (Tucker-Davies Technologies). Spike data were sampled at 24414 Hz and LFP data at 1017 Hz. ZIF-clip-based analog headstages with a unity gain and high impedance (~1 GΩ) were used. Threshold for spiking activity was set on-line using a Standard deviation of 4.5 (calculated over a 1 minute period using the TDT-RZ2 system), and waveforms and timestamps were stored for any event that crossed that threshold. Sorting was performed using TDT software (both on-line using Spike-Pac followed by off-line sorting using Offline Sorter), using a PCA-based method. We included both clearly identified single-units and multi-unit activity for this analysis (results were pooled as there were not clear differences in single and multi-unit responses). A total of 103 single and multi-units were recorded from healthy animals, 396 single and multi-units from animals post-stroke and 56 single units (only high SNR units were used in this experiment in order to ensure there was no contamination of neural activity from the stimulation artifact during the CS experiments. Behavior-related time-stamps (i.e., trial onset, trial completion) were sent to the RZ2 analog input channel using an Arduino digital board and synchronized to neural data.

Behavior

In stroke-studies, animals were acclimated and then trained to plateau level of performance (typically >75% accuracy) in a reach to grasp single pellet task before stroke induction and neural probe implantation. In healthy studies, animals were acclimated and underwent ~10-20 trials of the reach task in order to determine handedness prior to neural probe implantation. Stroke/probe implantation was performed contralateral to the preferred hand Animals were allowed to rest for 5 days before the start of experimental sessions. During this period, we closely monitored the animals and ensured that body weights did not drop below 95% of the initial weight. Reach sessions were typically conducted in the morning.

We used an automated reach-box, controlled by custom MATLAB scripts and an arduino micro-controller, that required minimal user intervention, as described previously (Wong et al., 2015). Each trial consisted of a pellet dispensed on the pellet tray; followed by an alerting beep indicating trial was beginning and then the door opening Animals then had to reach their arm out, grasp and retrieve the pellet. A real-time "pellet-detector" using an IR detector was used to determine when the pellet was moved, indicating the trial was over, and the door was closed. All trials were captured by video; and video was synced with electrophysiology data using Arduino digital output. Physiological data presented in this paper was time-locked to the onset of the reach movement. Direct Current Stimulation Studies Anesthetized Animals In micro-stimulation experiments conducted in anesthetized animals were anesthetized using a ketamine/xylazine cocktail (85 mg/kg ketamine, and 10 mg/kg xylazine), with supplemental ketamine given ~ every 40-60 minutes as needed to maintain a stable anesthetic level, and also to maintain anesthesia at stage III/3 characterized by predominantly slow oscillations(Friedberg et al., 1999). 0.05 mg/kg atropine was also given separately to help decrease secretions and counteract cardiac and respiratory depression caused by xylazine. After anesthesia and craniotomy was performed, epidural stimulation electrodes were implanted (using skull-screws embedded in the skull), in the configuration noted in FIG. 4. These screws were connected to a Multi-Channel Systems Stimulus Generator (MCS STG4000 series) to deliver direct-current stimulation. In 3 animals, ~2 mm tungsten wire was placed epidurally into the craniotomy well that delivered the electrical stimulation. 32-ch multi-electrode arrays were implanted into Layer 5 of motor cortex (1200-1500 uM deep). Single-unit and LFP activity was recorded for 1 hour to ensure stability of recordings and minimize drift during stimulation experiment. Then, we recorded a base-line period of neural activity (~15 minutes), followed by neural activity during direct-current stimulation (typically using 50-100 uA currents, applied for 5 minutes).

In Vivo Direct-Current Stimulation Experiments

For in-vivo experiments, after a stroke was induced (as described above), skull-screws were implanted in the configuration shown in FIG. 5. Animals were allowed to recover for 1 week, followed by motor testing several times per week to determine time course and extent of recovery. If animals continued to have persistent motor deficits, they were used for follow-up CS studies. Animals that had fully recovered after the first 1 week were excluded from further testing and monitoring (n=3). Direct-current stimulation was typically applied using an IZ2 stimulus isolator (TDT), with current pulses beginning 500 ms prior to the door opening (i.e. signal of trial starting), and ending after 2 seconds (i.e. when the trial ended). Two animals had longer trial-durations of up to 5 seconds. Stimulation intensity was focused and brief in order to maximally occur during the low-frequency oscillations that occur during reaching. Sessions were organized in groups of 30 trials; with "stimulation on" and "off" blocks occurring in immediate succession with each other Animals typically performed anywhere from 4-6 sessions/day. Current used for stimulation ranged from 50 to 200 uA.

Two different controls were performed to assess for specificity of this stimulation paradigm. First, a "sham" stimulation was performed, in which current was turned on for only 100 ms, and then turned off again. We also tested the efficacy of brief pulses of TACS (delivering box-car pulses at 10 and 100 hz).

Data Analysis

LFP and Single-Unit Analyses

Analyses were conducted using a combination of custom-written routines in MATLAB 2015A (The MathWorks), along with functions/routines from the EEGLAB toolbox and the Chronux toolbox. Pre-processing steps for LFP analysis included: artifact rejection (removing signals that were greater than 5 SD from the median); z-scoring; and median-normalization (at every time-point, the median signal across the 16 or 32 channels implanted in cortex was calculated; and this median signal was subtracted from every channel to decrease common noise and minimize volume conduction). Filtering of data at specified frequency bands was performed using the EEGLAB function eegfilt( ) Calculation of power and inter-trial phase-locking across frequencies was performed with wavelets using the EEGLAB function newtimef( ). Event-related power (as shown in FIG. 3B, 2E, and 3D) was calculated using wavelets, followed by Z-scoring for each trial (including data 4 seconds to 2.5 seconds after each reach). Changes in power and phase-locking were calculated by taking the mean/max power from −10 ms before to 500 ms after the reach started and calculating the inter-trial phase-locking across the first 50 and last 50 trials for each animal Calculation of principle components was performed using the MATLAB function pca( ) Principle-component trajectories were smoothed across 5 trials using the MATLAB function smooth. Calculation of spike-field coherence values was performed using the Chronux function mtcohgramcpb. For awake task-related experiments, SFC calculations were performed using a moving-window of 0.75-s segments. For SFC calculations in anesthetized experiments, we segmented the pre- and during-stimulation periods into 30-s segments and then averaged the coherency measures across segments.

Statistical Analysis

Parametric statistics were generally used in this study (ANOVA, t-tests and Pearson linear regression), implemented within either MATLAB or SPSS. In FIGS. 2 and 2, we calculated statistics across channels pooled from all animals (for power/phase-locking); single-units pooled across animals (spike-field coherence); or at the level of trials in each animal (for neural trajectory correlations). FDR correction for multiple comparisons was performed when time and or frequency was involved (i.e. for FIGS. 1b, 1e, 1f, 2d and 2g). In FIG. 4c, parametric statistics were used at the level of single units (for spike-field coherence), or animals (in the case of power modulation). In FIG. 5d, parametric statistics were calculated at the level of experimental sessions.

Although the present invention has been described with reference to preferred embodiments, persons skilled in the art will recognize that changes may be made in form and detail without departing from the spirit and scope of the invention.

What is claimed is:

1. A neurostimulation system for promoting subject recovery from a brain lesion, the neurostimulation system comprising:
   a. at least one electrode; and
   b. an operations system in electrical communication with the at least one electrode,
   wherein the at least one electrode and the operations system are constructed and arranged to:
   i. record low frequency oscillations from a perilesional region of the subject; and
   ii. apply current stimulation across the brain of the subject in phase with the recorded perilesional low frequency oscillations of less than 4 Hz.

2. The system of claim 1, wherein the applied current is direct current stimulation.

3. The system of claim 1, wherein the applied current is alternating current stimulation.

4. The system of claim 3, wherein alternating current stimulation is delivered at between about 0.1 and about 1000 Hz.

5. The system of claim 1, wherein the operations system is constructed and arranged to apply current in response to recorded electrical activity.

6. The system of claim 1, wherein the operations system is constructed and arranged to deliver current in response to subject movement.

7. A method for promoting recovery from a stroke induced loss of motor function in a subject comprising:
   a. placing at least one recording electrode in electrical communication in a perilesional region of the subject;
   b. placing at least one stimulation electrode in electrical communication with the brain of the subject;
   i. recording low frequency oscillations from the perilesional region of the subject; and
   ii. delivering current stimulation to the brain of the subject in phase with the recorded perilesional low frequency oscillations of less than 4 Hz.

8. The method of claim 7, wherein the current stimulation is delivered by direct current stimulation.

9. The method of claim 7, wherein the current stimulation is delivered by alternating current stimulation.

10. The method of claim 1, wherein the delivery of alternating current stimulation is concurrent with a peak of a low frequency oscillation waveform.

11. The method of claim 7, further comprising instructing the subject to perform a motor task.

12. The method of claim 11, wherein current delivery is about 500 ms prior to onset of performance of the motor task by the subject.

13. The method of claim 11, wherein current delivery is triggered by concurrence of task performance and low frequency oscillation detection.

14. The method of claim 7, wherein current is delivered to the perilesional region of the subject.

15. The method of claim 14, further comprising placing one or more stimulation electrodes in one or more of the basal ganglia, brainstem, cerebellum or thalamus of the subject.

16. The method of claim 7, wherein the recording electrode and stimulating electrode are cranial screws.

17. A neurostimulation system for improving recovery in a subject with a brain lesion, the neurostimulation system comprising:
   a. an electrode; and
   b. an operations system,
   wherein the electrode and operations system are constructed and arranged to deliver current to the brain of the subject in phase with low frequency oscillations and in response to low frequency oscillations of less than 4 Hz in the perilesional region of the subject's brain.

18. The neurostimulation system of claim 17, further comprising at least one electromyography electrode, constructed and arranged to record muscle movement of the subject and the operations system delivers current to the brain of the subject upon co-occurrence of perilesional low frequency oscillations and subject muscle movement.

* * * * *